United States Patent [19]

Shapiro et al.

[11] Patent Number: 5,188,823
[45] Date of Patent: Feb. 23, 1993

[54] ANTIPERSPIRANT FORMULATIONS

[75] Inventors: Irene Shapiro, Buffalo Grove; Branko Sajic, Chicago, both of Ill.

[73] Assignee: Stepan Company, Northfield, Ill.

[21] Appl. No.: 651,960

[22] Filed: Feb. 7, 1991

[51] Int. Cl.$^5$ ............... A61K 7/34; A61K 7/38; A61K 9/10
[52] U.S. Cl. ............... 424/65; 424/DIG. 5; 424/47; 424/68; 424/67; 514/938
[58] Field of Search .............. 564/156; 424/66, 68

[56] References Cited

U.S. PATENT DOCUMENTS

| | | | |
|---|---|---|---|
| 2,294,878 | 9/1942 | Hummel et al. | 564/156 |
| 4,777,035 | 10/1988 | Shin | 424/66 |
| 4,851,214 | 7/1989 | Walters et al. | 424/68 |
| 5,015,415 | 5/1991 | Goze et al. | 424/70 |

OTHER PUBLICATIONS

Cosmetics & Toiletries, Dec. 1985, vol. 100, No. 2, pp. 27 to 31, 33 and 35, Fox.
Cosmetics & Toiletries, vol. 100, Dec. 1985, pp. 65, 68, 69, 72, 73, 74 and 75.

Primary Examiner—Dale R. Ore
Attorney, Agent, or Firm—Allegretti & Witcoff, Ltd.

[57] ABSTRACT

Anhydrous and water-in-oil antiperspirant formulations are disclosed comprising effective suspending amounts of a compound of the formula:

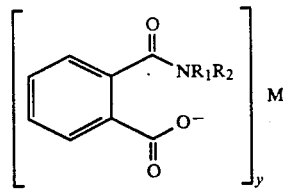

wherein
$R_1$ and $R_2$ are independently selected from the group consisting essentially of H or $C_1$-$C_{40}$ linear or branched, substituted or unsubstituted alkyl, cycloalkyl, alkylene, alkaryl, aryl or $R_3$-O-$R_4$ groups, with $R_3$ and $R_4$ being independently selected from the group consisting essentially of $C_1$-$C_{22}$ linear or branched, substituted or unsubstituted alkyl, cycloalkyl, alkylene, alkaryl and aryl groups;
y is an integer of a value satisfying the valency of M; and
M is a cation, preferably selected from the groups comprising $H^+$, $Na^+$, $K^+$, $Ba^{++}$, $Ca^{++}$, $Mg^{++}$, $Al^{+++}$, $Ti^{+++}$, $Zn^{++}$, $NH_4^+$, $R_5R_6R_7 N^+H$ wherein $R_5$, $R_6$ and $R_7$ are the same or different and are selected from the groups comprised of H, $C_1$-$C_{20}$ linear or branched, substituted or unsubstituted alkyl, alkylene, aryl straight or branched chain alkyl or alkylene $C_1$-$C_{40}$ groups or $R_8$-O-$R_9$ groups with $R_8$ and $R_9$ being independently selected from the groups comprised of $C_1$-$C_{22}$ linear or branched, substituted or unsubstituted alkyl, cycloalkyl, alkylene, alkaryl and aryl groups, and mixtures thereof.

Methods are also disclosed for preparing anhydrous and water-in-oil antiperspirant formulations.

19 Claims, No Drawings

ANTIPERSPIRANT FORMULATIONS

BACKGROUND OF THE INVENTION
1. Field of the Invention

This invention relates to antiperspirant formulations and more particularly to stable antiperspirant formulations containing improved emulsifying/suspending agents.
2. Description of the Related Art Most common antiperspirant products are classified as either oil-in-water (o/w) emulsion systems or anhydrous suspension systems. Most antiperspirant emulsion systems contain effective amounts of nonionic emulsifying agents, about 20% active antiperspirant salt and as much as 70-75% water. Common consumer complaints associated with this type of antiperspirant product include excessive wetness and cooling effects upon application, long drying periods, and tackiness during drydown and a white residue after application.

Anhydrous systems typically contain about 20% active antiperspirant salt about 10-20% other additives such as emollients, talc, etc., and as high as 60-70% volatile/non-volatile silicone fluids. These anhydrous products have improved application properties, velvety after-feel, etc., but are expensive due to their high content of silicone. Antiperspirant compositions adapted for roll-on-application are known and include such compositions as are described for example, in British patent application No. GB 2018590A. Such antiperspirant compositions are substantially anhydrous and comprise a powdered antiperspirant agent suspended by a traditional hydrophobic suspending agent, such as bentonite clay, in a liquid hydrophobic volatile silicone vehicle (generally 60 to 95% by weight). Additionally, such compositions, containing less than about 4% of other hydrophobic materials, such as emollients, are typically less volatile than the silicone fluids.

In addition, U.S. Pat. No. 4,268,499 describes antiperspirant emulsion compositions which comprise an aqueous solution of an astringent agent; a volatile, water-soluble liquid; a polydiorganosiloxane-polyoxyalkylene copolymer; an oil-in-water type surfactant; and a water-in-oil type surfactant. U.S Pat. No. 4,499,069 discloses antiperspirant emulsions which contain an antiperspirant salt of aluminum and/or zirconium, volatile cyclic silicone, water, and a low pH-stable emulsifier mixture of polyethylene glycol stearyl ether and a lipophilic co-emulsifier such that the HLB of the emulsifier mixture is more than 7.5 and less than 9.9.

Common suspending agents or rheological additives that have been used in roll-on anhydrous antiperspirant formulations include hydrophobic agents such as colloidal silica and montmorillonite clays. However, such hydrophobic agents require the use of polar additives, such as propylene carbonate, to render the suspending agent functional. Further, various disadvantages are associated with the use of montmorillonite clays in anhydrous antiperspirant formulations. Among these disadvantages are the requirements that high shear equipment be used during the antiperspirant preparation. Further, the resulting preparations still exhibit whitening on the user's skin and exhibit changes in viscosity over time.

Various phthalamate derivatives have been suggested as being useful in plant growth regulator formulations, insect repellent formulations, bactericidal, fungicidal and/or herbicidal formulations, additives for improving low temperature flow characteristics of petroleum distillate fuels, solvent extraction formulations for certain heavy metal ions, additives for thermal recording materials, thickeners for silicone grease and oil-based drilling muds, additives for water-insensitive coatings, plasticizers, etc. Phthalamic acids or phthalamate derivatives have also been used as additives for insecticidal compositions; additives for vulcanization activators; additives for rust and corrosion inhibitor formulations; additives for screen-clogging prevention and rust inhibition formulations; additives in catalyst systems for polyurethane foam formulations, etc.

Further, certain ammonium phthalamates have been used as additives in fuel oil compositions, blending agents for greases, lubricating oil additives, and thickening agents for lubricating oil compositions. These ammonium phthalamates have the general formula:

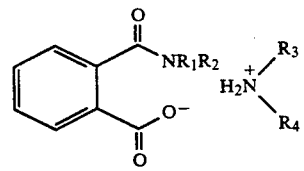

wherein $R_1$, $R_2$, $R_3$ and $R_4$ are $C_{16}$-$C_{40}$, preferably $C_{16}$-$C_{24}$ straight chain alkyl groups and may be the same or different.

Tallow is a fatty acid byproduct of the meat-packing industry obtained by rendering the body fat from cattle, horses and sheep. Tallows from different sources vary in free fatty acid content. The fatty acids normally found in tallow are various amounts of myristic acid, palmitic acid, stearic acid, oleic acid, and linoleic acid.

Several methods are known for the preparation of tallow amines, but a common method in industry is the conversion of a fatty acid to a nitrile by treatment with ammonia, followed by catalytic hydrogenation of the nitrile to primary, secondary, or tertiary amine by suitable adjustment in the reaction conditions. Tallow amines, as well as di(hydrogenated tallow) amine, are commercially available; for example, di(hydrogenated) tallow amines are available under the trade name ARMEEN ® 2HT (Akzo Chemicals, Chicago, Ill.).

Various routes exist for the preparation of phthalamic acids and phthalamic acid salts. In U.S. Pat. No. 4,402,708, N,N-diarachidyl phthalamic acid was prepared by adding phthalic anhydride to a 40% solution of a fatty amine in toluene in a 1:1 mole ratio at 80° C. The product was recovered by vacuum drying at 50° C. 0.05 mmHg for 20.5 hours. It was reported that phthalic anhydride sublimation was observed.

U.S. Pat. No. 4,402,708 also describes a method for preparing N,N-dioctadecyl phthalamic acid dioctadecyl ammonium salt and N,N-diarachidyl phthalamic acid diarachidyl ammonium salt. Phthalic anhydride was added to a 10% solution of select fatty amines in toluene in an anhydride to amine mole ratio of 1:2. The product was recovered by filtering and film evaporating a 1:1 toluene/n-heptane solution at 55° C., 40 mmHg.

Phthalamic acids have also been prepared by melting phthalic anhydride at about 131° C. and subsequent addition of molten secondary amine. The reactants were added in an equimolar ratio. At the temperature used in this method, 131° C. excessive phthalic anhydride sublimation occurs and increased product degradation was observed.

Phthalamic acids have also been prepared by addition of a solution of secondary fatty amines in isopropanol at about 78° C. to a phthalic anhydride/isopropanol slurry in a 1:1 phthalic anhydride/amine molar ratio with subsequent vacuum stripping of the solvent. This method utilizes isopropanol as the solvent for the reaction. Isopropanol, a secondary alcohol, reacts with phthalic anhydride to yield the isopropyl mono ester of phthalic acid. At 78° C., as much as 40% of the product may be an ester.

Attention is also directed to co-pending Goze et al. application 07/391,187, now abandoned and Goze et al. 07/542,780, now U.S. Pat. No. 5,015,415 both of which are incorporated herein by reference.

SUMMARY OF THE INVENTION

The present invention provides antiperspirant formulations comprising an effective emulsifying/suspending amount of a compound of the general formula:

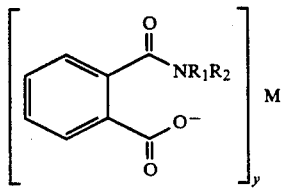

wherein $R_1$ and $R_2$ are independently selected from the group consisting essentially of H or $C_1$-$C_{40}$ linear or branched, substituted or unsubstituted alkyl, cycloalkyl, alkylene, alkaryl, aryl or $R_3$-O-$R_4$ groups, with $R_3$ and $R_4$ being independently selected from the group consisting essentially of $C_1$-$C_{22}$ linear or branched, substituted or unsubstituted alkyl, cycloalkyl, alkylene, alkaryl and aryl groups;

y is an integer of a value satisfying the valency of M; and

M is a cation, preferably selected from the groups comprising $H^+$, $Na^+$, $K^+$, $Ba^{++}$, $Ca^{++}$, $Mg^{++}$, $Al^{+++}$, $Ti^{+++}$, $Zn^{++}$, $NH_4^+$, $R_5R_6R_7N^+H$ wherein $R_5$, $R_6$ and $R_7$ are the same or different and are selected from the groups comprised of H, $C_1$-$C_{20}$ linear or branched, substituted or unsubstituted alkyl, alkylene, aryl straight or branched chain alkyl or alkylene $C_1$-$C_{40}$ groups or $R_8$-O-$R_9$ groups with $R_8$ and $R_9$ being independently selected from the groups comprised of $C_1$-$C_{22}$ linear or branched, substituted or unsubstituted alkyl, cycloalkyl, alkylene, alkaryl and aryl groups, and mixtures thereof.

The present invention also provides anhydrous antiperspirant formulations which exhibit very little, if any, viscosity changes over time.

The present invention further provides anhydrous antiperspirant formulations which may be prepared with or without the use of high shear equipment and with or without the use of polar additives.

The present invention provides antiperspirant formulations, such as roll-on, stick or spray products, which have excellent drying times and are non-tacky, non-oily, and non-whitening after application.

In addition, the present invention also provides anhydrous and water-in-oil antiperspirant formulations that exhibit excellent stability over time and at various temperatures.

DETAILED DESCRIPTION OF THE INVENTION

It has been discovered that when antiperspirant formulations are prepared with certain phthalamic acids or phthalamic acid salts as primary emulsifying/suspending agents, the resultant formulations exhibit improved stability and cosmetic properties over prior art water based or anhydrous antiperspirant formulations. In addition, formulations produced in accord with the principles of the invention are more readily manufactured than are prior art water based or anhydrous formulations In the antiperspirant formulations of the present invention, the phthalamic acids and salts unexpectedly function as primary emulsifying/suspending agents for active antiperspirant ingredients. In CTFA (Cosmetics, Toiletry and Fragrance Association) nomenclature, phthalamic acids may be designated as di(hydrogenated) tallow phthalic acid amides. However, they may also be designated as amido carboxy benzoic acids, and phthalamic acid salts may be designated amido carboxy benzoates.

It has also been discovered that the inventive water-in-oil antiperspirant formulations exhibit improved shelf-stability and improved cosmetic properties. Oil-in-water antiperspirant formulations are known and in comparison, the water-in-oil antiperspirant formulations of the present invention are superior Accordingly, the present invention encompasses antiperspirant formulations comprising effective suspending amounts of compounds of the formula:

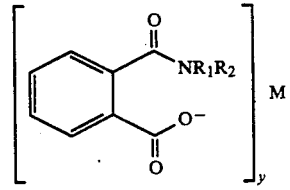

wherein $R_1$ and $R_2$ are independently selected from the group consisting essentially of H or $C_1$-$C_{40}$ linear or branched, substituted or unsubstituted alkyl, cycloalkyl, alkylene, alkaryl, aryl or $R_3$-O-$R_4$ groups, with $R_3$ and $R_4$ being independently selected from the group consisting essentially of $C_1$-$C_{22}$ linear or branched, substituted or unsubstituted alkyl, cycloalkyl, alkylene, alkaryl and aryl groups;

y is an integer of a value satisfying the valency of M; and

M is a cation, preferably selected from the groups comprising $H^+$, $Na^+$, $K^+$, $Ba^{++}$, $Ca^{++}$, $Mg^{++}$, $Al^{+++}$, $Ti^{+++}$, $Zn^{++}$, $NH_4^+$, $R_5R_6R_7N^+H$ wherein $R_5$, $R_6$ and $R_7$ are the same or different and are selected from the groups comprised of H, $C_1$-$C_{20}$ linear or branched, substituted or unsubstituted alkyl, alkylene, aryl straight or branched chain alkyl or alkylene $C_1$-$C_{40}$ groups or $R_8$-O-$R_9$ groups with $R_8$ and $R_9$ being independently selected from the groups comprised of $C_1$-$C_{22}$ linear or branched, substituted or unsubstituted alkyl, cycloalkyl alkylene, alkaryl and aryl groups and mixtures thereof.

The antiperspirant formulations of the present invention may be anhydrous or water-in-oil formulations and may be in the form of roll-on, stick or spray-on products. The phthalamic acids and/or phthalamic acid salts of the invention may be employed in any type of antiperspirant formulation. The phthalamic acids and/or salts function as effective primary emulsifying/suspending agents in water-in-oil formulations and in the anhydrous formulations prepared in accordance with the principles of the present invention.

The anhydrous antiperspirant formulations of the invention may be prepared to contain only effective amounts of active antiperspirant agents, at least one silicone fluid or compound, and a phthalamic acid and/or phthalamic acid salt. The anhydrous antiperspirant formulations of the present invention may optionally also contain other common ingredients, such as montmorillonite clays, perfumes, preservatives, antimicrobial agents, talc, emollients, etc.

Phthalamic acids and/or phthalamic acid salts may also be utilized to prepare water based or water-in-oil antiperspirant formulations. The water-in-oil formulations of the present invention comprise effective amounts of a phthalamic acid and/or salt as a primary emulsifying agent, a volatile silicone, an active antiperspirant salt and water. Preferred water-in-oil formulations may also include certain secondary emulsifying agents such as copolyols to further stabilize the water-in-oil emulsion.

Phthalamic Acids and/or Phthalamic Acid Salts

Various phthalamic acids, phthalamic salts and mixtures thereof may be employed in the present invention. These acids and/or salts have the following general formula:

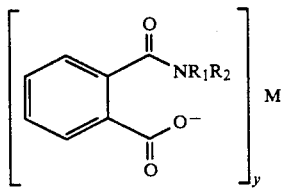

wherein
$R_1$ and $R_2$ are independently selected from the group consisting essentially of H or $C_1$–$C_{40}$ linear or branched, substituted or unsubstituted alkyl, cycloalkyl, alkylene, alkaryl, aryl or $R_3$-O-$R_4$ groups, with $R_3$ and $R_4$ being independently selected from the group consisting essentially of $C_1$–$C_{22}$ linear or branched, substituted or unsubstituted alkyl, cycloalkyl, alkylene, alkaryl and aryl groups;
y is an integer of a value satisfying the valency of M; and
M is a cation, preferably selected from the groups comprising $H^+$, $Na^+$, $K^+$, $Ba^{++}$, $Ca^{++}$, $Mg^{++}$, $Al^{+++}$, $Ti^{+++}$, $Zn^{++}$, $NH_4^+$, $R_5R_6R_7N^+H$ wherein $R_5$, $R_6$ and $R_7$ are the same or different and are selected from the groups comprised of H, $C_1$–$C_{20}$ linear or branched, substituted or unsubstituted alkyl, alkylene, aryl straight or branched chain alkyl or alkylene $C_1$–$C_{40}$ groups or $R_8$-O-$R_9$ groups with $R_8$ and $R_9$ being independently selected from the groups comprised of $C_1$–$C_{22}$ linear or branched, substituted or unsubstituted alkyl, cycloalkyl, alkylene, alkaryl and aryl groups, and mixtures thereof.

Representative phthalamic acids and/or salts are, for example, sodium soya amido benzoate, sodium oleyl amido benzoate, potassium dicoco amido benzoate, sodium stearyl amido benzoate, N,N-di(hydrogenated) tallow phthalamic acid, N,N-di(hydrogenated) tallow phthalamic acid N,N-di(hydrogenated) tallow ammonium salt and mixtures thereof. Representative phthalamic acids and/or salts are commercially available from Stepan Company (the assignee of the present invention).

In preferred embodiments of the antiperspirant formulations of the present invention, $R_1$, $R_2$, $R_5$, and $R_6$ are derived from hydrogenated tallow or stearyl fatty chains. The phthalamic acids and/or the salts thereof used in the present invention may have R groups that are the same or different. In a preferred embodiment the phthalamic material is a mixture of acid and salt in a ratio of about 90:10 to about 10:90. A presently preferred material is a mixture comprised of N,N-di(hydrogenated) tallow phthalamic acid and N,N-di(hydrogenated) tallow phthalamic acid N,N-di(hydrogenated) tallow ammonium salt.

Antiperspirant Salts

The antiperspirant salts of aluminum and/or zirconium may be selected from the various known materials of this nature. Suitable materials for use in both anhydrous and water-in-oil formulations are, for example, aluminum chloride, aluminum chlorhydroxide, basic aluminum bromide, zirconyl chloride, zirconyl hydroxide, complexes of aluminum hydroxide, zirconyl chloride and aluminum chlorhydroxide, complexes of aluminum hydroxide, zirconyl hydroxychloride and aluminum chlorhydroxide, complexes of dihydroxyaluminum glycinate, zirconyl chloride and/or zirconyl hydroxychloride and aluminum chlorhydroxides, complexes of zirconyl chloride and/or zirconyl hydroxychloride with aluminum chlorhydroxide and an amino acid, such as glycine (as a buffering agent), and mixtures of two or more of the above. The antiperspirant used is generally soluble in water, but insoluble in the silicone material, which is hydrophobic. The amount of antiperspirant present may be varied to suit particular needs. In general, the formulations will comprise from about 2 to 30% antiperspirant salt by weight, and preferably from about 10 to 25% antiperspirant salt. There must be enough of the active antiperspirant material present for the formulation to be effective as an antiperspirant. On the other hand it is expected that concentrations above about 20–30% of antiperspirant salt may be outside present regulatory limits. (As used herein the antiperspirant salt concentrations are based upon equivalent amounts of the particular hydrated salt). A particularly effective antiperspirant salt, designated according to its Cosmetic, Toiletry and Fragrance Association (CTFA) adopted name is aluminum zirconium tetrachlorohydrex glycine, a coordination complex of aluminum zirconium tetrachlorohydrate and glycine, in which some of the water molecules normally coordinated to the metals have been displaced by glycine. These materials are available commercially, for example from Dow Corning, Inc. under the designation Dow Corning AZG 368, 369, 370, or 374.

Volatile Silicones

The volatile silicones which may be used in the formulations of the present invention are well known and have been generally taught to be useful in antiperspirant formulations. Generally such volatile silicones may be represented by the formula:

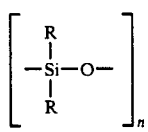

wherein R is a 1 to 3 carbon alkyl group, n is a number from 3 to 10, preferably from 3 to 7, and the unsatisfied valences on the oxygen and silicon atoms at the ends of the chain may be joined to one another to form a cyclic structure. Suitable volatile cyclic silicones are, for example, U.C.C. Y-7207 sold by Union Carbide Corporation in which each R is methyl and which typically comprises by weight 99.4% tetramer, 0 6% trimer and traces of the pentamer and hexamer; SWS-03314, sold by SWS Silicones, a Division of Stauffer Chemical Company, in which R is methyl and which is substantially all tetramer; and Dow Corning 344 fluid, sold by Dow Corning, Inc., in which R is methyl and which typically comprises by weight about 88% tetramer, about 11.8% pentamer and traces of trimer and hexamer. Typical vapor pressures of volatile cyclic silicones are shown below. These vapor pressures were determined using Dow Corning 344 fluid at various temperatures.

| Temperature | Vapor Pressure, mmHg |
|---|---|
| 26° C. | 1 |
| 64° C. | 10 |
| 77° C. | 20 |
| 92° C. | 40 |
| 101° C. | 60 |
| 114° C. | 100 |
| 155° C. | 400 |
| 178° C. | 760 |

In addition, other volatile silicones may also be utilized, alone or in combination with non-volatile silicones.

Copolyols

Copolyols may be utilized in the water-in-oil formulations of the present invention as secondary emulsifiers to stabilize the water-in-oil emulsions. Presently preferred copolyols include Q2-5200 (laurylmethicone copolyol), Abil B-9806 (cetyl dimethicone copolyol) and mixtures thereof. Other copolyols may also be useful.

Montmorillonite Clays

The montmorillonite clays that may be used in the anhydrous formulations of the present invention include montmorillonite clays such as Bentone 38 (known in CTFA momenclature as Quaternium-18 Hectorite) and Bentone 34 (known in CTFA nomenclature as Quaternium-18 Bentonite) as well as other suitable clays.

Anhydrous Antiperspirant Formulations

The anhydrous antiperspirant formulations of the invention may be prepared to contain only effective amounts of an active antiperspirant agent, at least one silicone, and a phthalamic acid, phthalamic acid salt or mixtures of acid and acid salt. The anhydrous antiperspirant formulations of the present invention may optionally also contain montmorillonite clays, as well as other commonly known ingredients.

The effective concentration of the phthalamic acid and/or salt in antiperspirant formulations of the present invention varies from about 0.1% up to about 30% on an active basis. A more preferred concentration is about 1% to about 20%.

In addition to the phthalamic acid and/or salt, anhydrous formulations of the present invention typically comprise from about 1% to about 30% of an active antiperspirant agent and from about 25% to about 90% of a suitable silicone.

In a particularly preferred embodiment of the present invention, the antiperspirant formulation comprises a mixture of N,N-di(hydrogenated tallow) phthalamic acid and N-N-di(hydrogenated) phthalamic acid N,N-di(hydrogenated) tallow ammonium salt. A particularly preferred antiperspirant formulation comprises a volatile silicone, a mixture of N,N-di(hydrogenated) tallow phthalamic acid and N-N-di(hydrogenated)tallow phthalamic acid N,N-di(hydrogenated) tallow ammonium salt, Bentone 38, and AlZr tetrachlorohydrex glycine. Suspending agents such as Bentone 38 are compatible with the phthalamic acids and/or salts of the invention. The formulations may also contain other additives such as talc or silica, perfumes, emollients, antimicrobial agents, etc.

The formulations of the present invention exhibit excellent homogeneity and substantially less separation than prior art antiperspirants prepared with equivalent amounts of montmorillonite clays. The formulations of the invention dry quickly leaving a velvety, silky afterfeel on the skin and do not leave any white residue The formulations in the present invention are stable at temperatures of about 5° C., 25° C., 42° C. and 50° C.

Examples of anhydrous antiperspirant formulations according to the present invention are shown in Table I. For purposes of comparison, prior art formulations were prepared essentially in accordance with the teaching of U.K. Patent GB 2018590B. These formulations are also shown in Table I as formulations 4, 5 and 6. The mixing procedure for the prior art formulations were identical to that for the formulations of the present invention shown in Table I. Table II shows a preferred formulation in accordance with the principles of the invention and prepared to include montmorillonite clay.

TABLE I

ANHYDROUS ANTIPERSPIRATION FORMULATIONS

Formulations with Amounts of % by weight of Total Formulations

| Ingredients | 1 | 2 | 3 | 4[1] | 5[1] | 6[1] | 7 | 8 | 9 | 10 | 11 |
|---|---|---|---|---|---|---|---|---|---|---|---|
| Silicone 344 (Cyclomethicone) | 74.0 | 72.0 | 70.0 | 74.0 | 72.0 | 70.0 | 71.0 | 69.0 | 67.0 | 74.0 | 74.0 |
| N,N-di(hydrogenated) tallow Amido Benzoic Acid and N,N-di(hydrogenated) tallow Amido Benzoic Acid N,N-di(hydrogenated) tallow | 6.0 | 8.0 | 10.0 | — | — | — | 3.0 | 3.0 | 3.0 | | |

TABLE I-continued

ANHYDROUS ANTIPERSPIRATION FORMULATIONS

| Ingredients | Formulations with Amounts of % by weight of Total Formulations | | | | | | | | | | |
|---|---|---|---|---|---|---|---|---|---|---|---|
| | 1 | 2 | 3 | 4[1] | 5[1] | 6[1] | 7 | 8 | 9 | 10 | 11 |
| ammonium Salt at an acid to salt ratio of about 55:45 | | | | | | | | | | | |
| N,N-diCoco Amido Benzoic acid and N,N-diCoco Amido Benzoic acid potassium salt at an acid to salt ratio of about 55:45 | — | — | — | — | — | — | — | — | — | 6.0 | — |
| N,N-di(hydrogenated) rapeseed (predominatly $C_{18}$ and $C_{22}$ fatty acids) Amido Benzoic Acid N,N-di(hydrogenated) Rapeseed Amido Benzoic Acid N,N-di (hydrogenated) Rapeseed Ammonium SAlt at an acid to salt ratio of about 55:45 | — | — | — | — | — | — | — | — | — | — | 6.0 |
| Dow Corning AZG 370 (tetrachlorohydrex Glycine) | 20.0 | 20.0 | 20.0 | 20.0 | 20.0 | 20.0 | 20.0 | 20.0 | 20.0 | 20.0 | 20.0 |
| Bentone Gel VS-5 (Cyclomethicone and Quaternium-18 Hectorite and SDA alcohol 40) | | | | 6.0 | 8.0 | 10.0 | 6.0 | 8.0 | 10.0 | — | — |

[1]Formulation Composition in accord with UK patent GB 2018590B

TABLE IA

EVALUATION OF ANHYDROUS FORMULATIONS

| Formulation | % Separation by Weight | Form[1] | Viscosity[2] (cps) |
|---|---|---|---|
| 1 | 1% | Liquid | 2,800 |
| 2 | minimal | light cream | 3,800 |
| 3 | none | cream | 4,200 |
| 4 | 11% | liquid | 400 |
| 5 | 8% | liquid | 1,000 |
| 6 | 7% | liquid | 1,100 |
| 7 | 5% | liquid | 800 |
| 8 | none | light cream | 5,800 |
| 9 | none | light cream | 6,200 |
| 10 | 1-2% | cream | 2,300 |
| 11 | minimal | liquid | 1,600 |

[1]Formulations evaluated 24 hours at room temperature after preparation.
[2]Viscosity measured with a Brookfield RVF, spindle, No. 4, speed at 20 RPM, for 1 minute.

As can be seen from the above data, formulations 1 2, 3, 7, 8, 9, 10 and 11 are in accord with the principles of the invention. These formulations exhibited minimal separation and varied in form from liquid to light cream with viscosities ranging from about 800 cps to about 4,200 cps, rendering them suitable for roll-on, stick or spray-on product forms. On the other hand, formulations 4, 5 and 6, containing similar amounts of silicone and antiperspirant as the above inventive formulations, but containing no am benzoic acids and/or salt mixtures and only a prior art montmorillonite clay as a suspending agent, exhibited a considerable amount of separation and had a relatively low range of viscosity.

TABLE II

EXEMPLARY ANHYDROUS FORMULATION

| Ingredients | Formulation with amounts as % by weight of total Formulation |
|---|---|
| 1. Silicone 344 (Cyclomethicone) | 72.0 |
| 2. N,N-di(hydrogenated) tallow Amido Benzoic Acid and N,N-di(hydrogenated) tallow Amido Benzoic Acid N,N-di(hydrogenated) tallow Ammonium Salt at an acid to salt ratio of about 70:30 | 4.0 |
| 3. Dow Corning AZG 370 (AlZr Tetrachlorohydrex Glycine) | 22.0 |
| 4. Talc 1626 | 1.0 |
| 5. Octyl Isononanoate | 1.0 |
| | 100.00 |

Water-in-Oil Antiperspirant Formulations

The water-in-oil formulations of the present invention comprise a phthalamic acid and/or salt as an emulsifying/suspending agent, at least one silicone, and an active antiperspirant salt. Preferred water-in-oil formulations may include certain copolyols to further stabilize the water-in-oil emulsion. The water-in-oil formulations have a silicone/phthalamic acid and/or salt external phase and an active antiperspirant ingredient dispersed within the internal water phase. These water-in-oil formulations exhibit improved application properties, and superior drying times and are non-tacky, non-oily, and non-whitening after application. In addition, the water-in-oil formulations of the invention are less costly than prior art anhydrous formulations.

Certain preferred embodiments of the present invention comprise a water-in-oil formulation comprising about 0.1% up to about 30% of a phthalamic acid and/or salt and about 0.1% to about 10% of a copolyol. More preferred formulations comprise about 1% to about 20% of a phthalamic acid and/or salt and about 0.5% to 5% copolyol.

Representative water-in-oil phthalamic acid and/or salt formulations of the present invention are shown in Table III. For purposes of comparison water-in-oil prior art formulations were prepared; their compositions are also shown in Table III as formulations 15 and 16. These prior art formulations exhibited separation after 3 days at about 50° C. (120° F.). The water-in-oil formulations of the present invention clearly yield improved stability over the prior art formulation. The comparison of physical properties is shown in Table IIIB.

TABLE III

WATER-IN-OIL FORMULATIONS

| | Formulations with Amounts as % by weight of Total Formulations | | | | |
|---|---|---|---|---|---|
| Ingredients Formulations | 12 | 13 | 14 | 15* | 16 |
| Silicone 344 (Cyclomethicone) | 32 | 30 | 22.5 | 27 | 32.5 |
| N,N-di(hydrogenated) tallow Amido Benzoic Acid and N,N-di(hydrogenated) tallow Amido Benzoic Acid N,N-di(hydrogenated) tallow Ammonium Salt at an acid to salt ratio of about 30:70 | 0.5 | 2.5 | 10 | — | — |
| Abil B-9806 (Cetyl Dimethicone Copolyol) | 3 | 3 | 3 | — | 3 |
| Dow Corning AZH 368, 31% sol. (AlZr tetrachlorhydrex Glycine) | 64.5 | 64.5 | 64.5 | 40 | 64.5 |
| D.I. Water | Q.S. | Q.S. | Q.S. | Q.S. | Q.S. |
| 3225C Formulation Aid (Cyclomethicone and Dimethicone Copolyol) | — | — | — | 6.0 | — |
| Polysorbate 20 | — | — | — | 1.0 | — |

*Formulation Composition page 52, "Happi", Vol. 23, No. 2, Feb. 1986

TABLE IIIA

EVALUATION OF WATER-IN-OIL

| Formulation | Form | 3 days 50° C. | 2 wk. at 25° C. | 2 wk at 42° C. | 2 wk. at 50° C. |
|---|---|---|---|---|---|
| 12 | Liq. | stable | stable | not stable | not stable |
| 13 | Liq. | stable | stable | stable | stable |
| 14 | Paste | stable | stable | stable | stable |
| 15 | Liq. | not stable | not stable | not stable | not stable |
| 16 | Liq. | separate immediately | separate immediately | separate immediately | separate immediately |

TABLE IIIB

COMPARATIVE EVALUATION*

| | Cooling Effect | Tackiness | Drying Time | Whitening |
|---|---|---|---|---|
| FORMULATION 13 | 3 | 3 | 3 | 5 |
| PRIOR ART FORMUALTION "A" (U.S. Pat. No. 4,499,069) | 1-2 | 2 | 1-2 | 0-1 |

*Value ratings: Average value assigned by a 1- member panel in blind tests with 0 = very poor performance; 1 = poor performance; 2 = slightly better; 3 = noticeable different; 4 = obvious difference; 5 = excellent
Cooling effect: Perceived sticky feel, apparently due to relatively high amount of water and antiperspirant salt.
Drying time: Observed period of time until volatile silicone and water evaporated from applied layer of antiperspirant product
Whitening: Observed amount of white residue left on skin after drying period.

As can be seen from the above comparative evaluation, the antiperspirant water-in-oil emulsion product of the invention was superior in all tested categories against a similar prior art product. In addition, antiperspirant water-in-oil emulsion products produced in accord with the principles of the invention exhibited almost no visible white residue after drying.

TABLE IV

WATER-IN-OIL FORMULATIONS

| | Ingredients | Formulations with amounts As % Weight of Total Formulation | | | |
|---|---|---|---|---|---|
| | | 17 | 18 | 19 | 20 |
| 1 | Silicone 344 (Cyclomethicone) | 30.0 | 30.0 | 30.0 | 30.0 |
| 2a | Sodium Soya (predominantly $C_{18}$ polyunsaturated fatty acids) Amido Benzoate | 2.5 | — | — | — |
| 2b | Sodium Oleyl (predominantly $C_{18}$ monosaturated fatty acids) Amido Benzoate | — | 2.5 | — | — |
| 2c | N,N-Dicoco (predominantly $C_{14}$-$C_{14}$ fatty acids) Amido Benzoate and Potassium dicoco Amido Benzoate at an acid to salt ratio at about 55:45 | — | — | 2.5 | — |
| 2d | N,N-di(hydrogenated) rapeseed (predominantly $C_{18}$ and $C_{22}$ fatty acids) Amido Benzoic acid and N,N-di(hydrogenated) rapeseed amido benzoic acid N,N-di(hydrogenated) rapeseed ammonium salt at an acid to salt ratio of about 55:45 | — | — | — | 2.5 |
| 3 | Abil B-9806 (Cetyl Dimethicone Copolyol) | 3.0 | 3.0 | 3.0 | 3.0 |
| 4 | Dow Corning AZG 368 (31% sol.) AlZr tetrachlorohydrex Glycine) | 64.5 | 64.5 | 64.5 | 64.5 |
| 5 | Water | Q.S | Q.S | Q.S | Q.S |

EVALUATION

| Form | Liq. | Liq. | Paste | Liq. |
|---|---|---|---|---|
| Viscosity* | 2,700 cps | 3,600 cps | 14,000 cps | 2,900 cps |
| 60 day Stability at: | | | | |
| R. Temp. | stable | stable | stable | stable |
| 50° C. (120° F.) | stable | stable | stable | stable |
| 42° C. (108° F.) | stable | stable | stable | stable |

*Viscosity measured at room temperature with a Brookfield RUF, spindle No. 4, at speed of 20 RPM for 1 minute.

As can be seen from the above formulations shown in Tables III, IIIA, IIIB and IV, formulations prepared in accord with the principles of the invention are stable over prolonged periods of time and varying temperature conditions. Note prior art formulation No. 15 separated after only 3 days at 50° C. while formulations 12, 13, 14 and 17, 18 and 19 remained stable for at least 14 and 60 days at temperatures ranging from about room temperature (25° C.) up to about 50° C. and exhibited viscosities suitable for roll on, cream, and spray-on products. Further, formulations 17, 18 and 19 demonstrate that alkylene fatty mono amates as well as fatty polyalkylene amates may be advantageously utilized.

The present invention also encompasses methods for preparing the water-in-oil antiperspirant formulations of the present invention. These methods comprise the steps of;
(a) preparing a water phase containing an antiperspirant salt;
(b) preparing an oil phase containing a phthalamic acid and/or phthalamic acid salt in at least one volatile silicone; and
(c) adding the oil phase to the water phase; and
(d) mixing the oil phase with the water phase and homogenizing such mixture to form a stable water-in-oil antiperspirant formulation.

The invention is illustrated further by the following examples which, like the previous examples, are not to be construed as limiting the invention in scope or spirit to the specific procedures described in them.

EXAMPLE I

Preparation of an Anhydrous Antiperspirant Formulation With a Phthalamic Acid/Salt Mixture Silicone 344 (Cyclomethicone) (70.0 g) and N,N-di(hydrogenated) Amido Benzoic acid and N,N-di(hydrogenated) tallow Amido Benzoic acid/N,N-di(hydrogenated) tallow ammonium salt (hereinafter STEPAN-TAB TM -2) (10.0 g) were added to a reaction vessel and heated to about 55°-57° C. Dow Corning AZG 370 (AlZr tetrachlorohydrex glycine) (20 g) was subsequently added and the mixture agitated for 15 minutes. This mixture was then cooled to about 32°-35° C. and subsequently homogenized. The resultant product, a stable antiperspirant formulation (formulation 3, Table I), was a cream having an initial viscosity of 4,200 cps and did not separate after 24 hours at room temperature.

EXAMPLE 2

Preparation of an Anhydrous Roll-On Antiperspirant Formulation with a Phthalamic Acid/Salt Mixture Silicone 344 (72 g) and STEPAN-TAB TM -2 (4 g) were added to a vessel and heated to about 55°-57° C. After the mixture cooled to about 32° C., Dow Corning AZG 370 (22 g), Talc 1626 (1 g) and octyl isononanoate (1 g) were added and the mixture was homogenized to yield a stable antiperspirant product, (exemplary formulation, Table II).

EXAMPLE 3

Preparation of an Anhydrous Antiperspirant Formulation Without a Phthalamic Acid or Salt Mixture Silicone 344 (Cyclomethicone) (70.0 g) and Bentone Gel VS-5 (cyclomethicone and Quaternium-18 Hectorite and SDA-40) (10.0 g) were added to a reaction vessel. Dow Corning AZG 370 (AlZr tetrachlorohydrex glycine) (20 g) was subsequently added and the mixture agitated for about 15 minutes. This mixture was homogenized. The resultant formulation (formulation 5, Table I) was a liquid having an initial viscosity of 1,000 cps. This liquid exhibited about 7% separation (by volume of total formulation volume) after 24 hours at room temperature.

EXAMPLE 4

Preparation of an Anhydrous Antiperspirant Formulation with a Phthalamic Acid/Salt and a Montmorillonite Clay Silicone 344 (70.0 g), STEPAN-TAB TM -2 (3.0 g) and Bentone Gel VS-5 (10.0 g) were added to a reaction vessel and heated to about 55°-57° C. Dow Corning AZG 370 (AlZr tetrachlorohydrex glycine) (20 g) was subsequently added and the mixture agitated for about 15 minutes. This mixture was cooled to about 32°-35° C. and subsequently homogenized. The resultant stable antiperspirant formulation (formulation 9, Tables I and IA) was a cream having a viscosity after 24 hours of 6,200 cps. This antiperspirant formulation exhibited no separation after 24 hours. The light cream product demonstrated excellent stability and rheological properties upon application.

EXAMPLE 5

Preparation of a Water-in-Oil Antiperspirant Formulation With a Phthalamic Acid/Salt Mixture Silicone 344 (30 g), STEPAN-TAB TM -2 (2.5 g) and Abil B-9806 (Cetyl Dimethicone Copolyol) (3.0 g) were added to a vessel and heated to about 55° C. to prepare an oil phase.

Dow Corning AZG 368, 31% solution (64.5 g) (AlZr tetrachlorohydrex glycine) was heated in a separate vessel to about 55° C. to prepare a water phase. When the water phase had reached a temperature of about 55° C., the oil phase was added to the water phase and this mixture was agitated for about 20-25 minutes. The mixture was cooled to 25°-30° C. and homogenized The resultant product (formulation 12, Table III) was a liquid that was stable at temperatures up to about 50° C. for two months.

EXAMPLE 6

Preparation of a Water-in-Oil Antiperspirant Formulation With a Phthalamic Acid/Salt An oil phase was prepared by blending 50 g of Silicone 344, 2.5 g STEPAN-TAB TM -2, and 3 g Abil B-9806 and was heated to about 55°-57° C.

A water phase was prepared by blending 20 g Dow Corning AZG 370 and 24.5 g distilled water and was heated to about 55° C.

The oil phase was subsequently added to the water phase and the mixture agitated for about 20-25 minutes. The product was cooled to about 20°-25° C. and homogenized. (Exemplary Formulation, Table IV).

EXAMPLE 7

Preparation of Water-in-Oil Antiperspirant Formulation Without a Phthalamic Acid/Phthalamic Acid Salt An oil phase was prepared by blending Silicone 344 (27 g). 3225° C. Formulation Aid (cyclomethicone and dimethicone copolyol, available from Dow Corning) (6.0 g), and Polysorbate 20 (1.0 g) and was heated to about 55° C. A water phase was prepared by blending Dow Corning AZG 368 (40 g) and water (26 g) and was heated to about 55° C. The water phase was subsequently added to the oil phase and mixed for about 20-25 minutes. The product was cooled to about 20°-25° C. (68°-77° F.) and homogenized. The resultant water-in-oil emulsion (formulation 13, Table III) separated after 3 days at a temperature of about 50° C.

From the foregoing it will be appreciated that, although specific embodiments of the invention have been described herein for purposes of illustration, various modifications may be made without deviating from the spirit and scope of the invention

What is claimed is:

1. An antiperspirant composition comprising an effective amount of a volatile silicone fluid, an effective amount of an antiperspirant salt, and an effective emulsifying and suspending amount of a compound of the formula

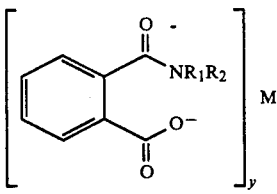

$R_1$ and $R_2$ are independently selected from the group consisting of H, $C_1$-$C_{40}$ linear alkyl, $C_1$-$C_{40}$ branched alkyl, cycloalkyl, $C_1$-$C_{40}$ linear alkylene, $C_1$-$C_{40}$ branched alkylene, alkaryl, aryl and $R_3$-O-$R_4$, with $R_3$ and $R_4$ being independently selected from the group consisting of $C_1$-$C_{22}$ linear alkyl, $C_1$-$C_{22}$ branched alkyl, cycloalkyl, $C_1$-$C_{22}$ linear alkylene, $C_1$-$C_{22}$ branched alkylene, alkaryl and aryl; y is integer of a value satisfying the valency of M; and M is a cation, consisting of $H+$, $Na+$, $K+$, $Ba++$, $Ca++$, $Mg++$, $Al+++$, $Ti+++$, $Zn++$, $NH_4+$, $R_5R_6R_7N+H$ wherein $R_5$, $R_6$ and $R_7$ are the same or different and are selected from the group consisting of H, $C_1$-$C_{20}$ linear alkyl, $C_1$-$C_{20}$ branched alkyl, $C_1$-$C_{20}$ linear alkylene, $C_1$-$C_{20}$ branched alkylene, aryl, $C_1$-$C_{40}$ straight chain alkyl, $C_1$-$C_{40}$ branched chain alkyl, $C_1$-$C_{40}$ straight chain alkylene, $C_1$-$C_{40}$ branched chain alkylene and $R_8$-O-$R_9$ with $R_8$ and $R_9$ being independently selected from the group consisting of $C_1$-$C_{22}$ linear alkyl, $C_1$-$C_{22}$ branched alkyl, cycloalkyl, $C_1$-$C_{22}$ linear alkylene, $C_1$-$C_{22}$ branched alkylene, alkaryl and aryl, and mixtures thereof.

2. The antiperspirant composition according to claim 1 wherein the amount of the compound in the formulation is about 0.1% to about 30%.

3. The antiperspirant composition according to claim 2, wherein the amount of the compound in the formulation is about 1% to about 20%.

4. An antiperspirant salt according to claim 3, wherein the amount of volatile silicone fluid in the formulation is about 10% to about 95%.

5. The antiperspirant composition according to claim 4, wherein the antiperspirant salt is selected from the group consisting of aluminum salts, zirconium salts and mixtures thereof.

6. The antiperspirant composition according to claim 5, wherein the amount of antiperspirant salt in the formulation is about 1% to about 30%

7. The antiperspirant composition according to claim 6, wherein the amount of the antiperspirant salt in the formulation is about 10% to about 25%.

8. The antiperspirant composition according to claim 7, further comprising at least one montmorillonite clay.

9. The antiperspirant composition according to claim 8, wherein the montmorillonite clay is a hydrophobic bentonite, hectonite or colloid magnesium aluminum silicate or mixtures thereof.

10. The antiperspirant composition according to claim 1, wherein y is 1, M is $H+$ and $R_1$ and $R_2$ are $C_{10}$-$C_{22}$ fatty alkyl, alkylene, aralkyl, or aryl groups.

11. The antiperspirant composition according to claim 1 wherein y is 1, M is $R_5R_6N+H_2$ and $R_1$, $R_2$, $R_5$, and $R_6$ are $C_{10}$-$C_{22}$ fatty alkyl, alkylene, aralkyl, or aryl groups.

12. The antiperspirant composition according to claim 1, wherein y is 1 M is $R_5R_6N+H_2$ and $R_1$, $R_2$, $R_5$ and $R_6$ are hydrogenated $C_{10}$-$C_{12}$ alkyl groups.

13. The antiperspirant composition according to claim 1 wherein the compound is selected from the group consisting of N,N-di(hydrogenated) tallow phthalamic acid, N,N-di(hydrogenated) tallow phthalamic acid N-N-di(hydrogenated) tallow ammonium salt and mixtures thereof.

14. The antiperspirant compound according to claim 1, wherein the compound is sodium soya amido benzoate.

15. The antiperspirant composition according to claim 1, wherein the compound is sodium oleyl amido benzoate.

16. The antiperspirant composition according to claim 1, wherein the compound is selected from the group consisting of N-N-dicoco amido benzoic acid, potassium N,N-dicoco amido benzoate and mixtures thereof.

17. The antiperspirant composition according to claim 1, wherein the compound is selected from the group consisting of N,N-di(hydrogenated)rapeseed amido benzoic acid, N,N-di(hydrogenated) rapeseed amido benzoic acid N,N-di(hydrogenated) rapeseed ammonium salt, and mixtures thereof.

18. A method for preparing a water-in-oil antiperspirant composition comprising the steps of:
(a) preparing a water phase containing an antiperspirant salt;
(b) preparing an oil phase containing a volatile silicone fluid and a compound of the formula:

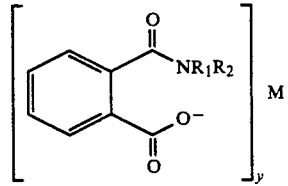

$R_1$ and $R_2$ are independently selected from the group consisting of H, $C_1$-$C_{40}$ linear alkyl, $C_1$-$C_{40}$ branched alkyl, cycloalkyl, $C_1$-$C_{40}$ linear alkylene, $C_1$-$C_{40}$ branched alkylene, alkaryl, aryl and $R_3$-O-$R_4$, with $R_3$ and $R_4$, being independently selected from the group consisting of $C_1$-$C_{22}$ linear alkyl, $C_1$-$C_{22}$ branched alkyl, cycloalkyl, $C_1$-$C_{22}$ linear alkylene, $C_1$-$C_{22}$ branched alkylene, alkaryl and aryl; y is an integer of a value satisfying the valence of M; and M is a cation, consisting of $H+$, $Na+$, $K+$, $Ba++$, $Ca++$, $Mg++$, $Al+++$, $Ti+++$, $Zn++$, $NH_4+$, $R_5R_6R_7N+H$ wherein $R_5$, $R_6$ and $R_7$ are the same or different and are selected from the group consisting of H, $C_1$-$C_{20}$ linear alkyl, $C_1$-$C_{20}$ branched alkyl, $C_1$-$C_{20}$ linear alkylene, $C_1$-$C_{20}$ branched alkylene, aryl, $C_1$-$C_{40}$ straight chain alkyl, $C_1$-$C_{40}$ branched chain alkyl, $C_1$-$C_{40}$ straight chain alkylene, $C_1$-$C_{40}$ branched chain alkylene and $R_8$-O-$R_9$ with $R_8$ and $R_9$ being independently selected from the group consisting of $C_1$-$C_{22}$ linear alkyl, $C_1$-$C_{22}$ branched alkyl, cycloalkyl, $C_1$-$C_{22}$ linear alkylene, $C_1$-$C_{22}$ branched alkylene, alkaryl and aryl, and mixtures thereof
(a) adding the oil phase to the water phase; and
(b) mixing the oil phase with the water phase to form water-in-oil antiperspirant composition.

19. The method according to claim 18, wherein the compound is selected from the group consisting of N,N-di(hydrogenated) tallow phthalamic acid, N,N-di(hydrogenated) tallow acid N,N-di(hydrogenated) tallow ammonium salt and mixtures thereof.

* * * * *